US012178988B2

(12) United States Patent
Goodin et al.

(10) Patent No.: US 12,178,988 B2
(45) Date of Patent: Dec. 31, 2024

(54) DISCREET HEALTH SYSTEM AND APPARATUS FOR INTRAVENOUS INFUSION EQUIPMENT

(71) Applicant: Mallory Design Group LLC, Greenfield, IN (US)

(72) Inventors: Andrew Goodin, Indianapolis, IN (US); Andrew Mundell, Indianapolis, IN (US); Amanda Bowling, Indianapolis, IN (US); Gregg Nowling, Indianapolis, IN (US)

(73) Assignee: MALLORY DESIGN GROUP LLC, Greenfield, IN (US)

( * ) Notice: Subject to any disclaimer, the term of this patent is extended or adjusted under 35 U.S.C. 154(b) by 0 days.

(21) Appl. No.: 18/104,698

(22) Filed: Feb. 1, 2023

(65) Prior Publication Data
US 2023/0241306 A1 Aug. 3, 2023

Related U.S. Application Data

(60) Provisional application No. 63/305,865, filed on Feb. 2, 2022.

(51) Int. Cl.
*A61M 5/14* (2006.01)
(52) U.S. Cl.
CPC .................. *A61M 5/1415* (2013.01)
(58) Field of Classification Search
CPC ............ A61M 5/1415; A61M 2205/59; A61M 5/1417; A61J 1/1462; F16M 11/28; A61G 12/001

USPC ........................................................ 248/125.8
See application file for complete search history.

(56) References Cited

U.S. PATENT DOCUMENTS

| 5,112,019 | A | | 5/1992 | Metzler et al. |
| D331,108 | S | * | 11/1992 | Curbbun ..................... D24/128 |
| 5,857,685 | A | * | 1/1999 | Phillips ................ A61M 5/1415 |
| | | | | 280/47.35 |
| 5,910,139 | A | * | 6/1999 | Cochran .................. H02H 3/12 |
| | | | | 606/1 |

(Continued)

OTHER PUBLICATIONS

Loughborough University; Jul. 2, 2018; IV Stand Designed To Reduce Anxiety For Children In Hospital; Full article and video at https://www.lboro.ac.uk/news-events/news/2018/july/student-designs-child-friendly-iv-stand/ (Year: 2018).*

(Continued)

*Primary Examiner* — Ingrid M Weinhold
(74) *Attorney, Agent, or Firm* — Indiana University Robert H. McKinney School of Law IP Clinic

(57) ABSTRACT

An arrangement for medical equipment configured to appear more desirable to the patient is provided. The present disclosure provides an arrangement of intravenous infusion equipment configured to appear as an ordinary household object. The arrangement of intravenous infusion equipment may be configured to appear as an object fitting into the patient's interests in order to make the patient more relaxed and comfortable. The arrangement of intravenous infusion equipment may be configured to appear as an object more desirable to the patient while the equipment is not in use and then extend into a more suitable position when the equipment is in use.

15 Claims, 5 Drawing Sheets

(56) References Cited

U.S. PATENT DOCUMENTS

| | | | | |
|---|---|---|---|---|
| 6,708,991 | B1* | 3/2004 | Ortlieb | A61M 5/1415 248/122.1 |
| 7,285,111 | B2* | 10/2007 | Gaster | A61M 5/1415 604/93.01 |
| 7,556,226 | B2* | 7/2009 | Muncie | A61M 5/1415 248/176.1 |
| 7,562,883 | B2* | 7/2009 | Livengood | A61H 3/04 280/43.24 |
| 10,039,992 | B2* | 8/2018 | Rivera | A61J 1/03 |
| 10,238,792 | B1* | 3/2019 | Macri | F16M 11/42 |
| 10,449,289 | B2* | 10/2019 | Ceccato | A45C 9/00 |
| 10,582,981 | B2* | 3/2020 | Childs | A61B 50/26 |
| 11,628,121 | B2* | 4/2023 | Casano | A61J 1/16 604/408 |
| 2005/0040126 | A1* | 2/2005 | Gaster | A61M 5/1415 211/207 |
| 2008/0054132 | A1* | 3/2008 | Muncie | A61M 5/1415 248/176.1 |
| 2015/0320929 | A1 | 11/2015 | Simonds | |
| 2016/0317392 | A1* | 11/2016 | Harris | A45F 3/04 |
| 2017/0296939 | A1* | 10/2017 | Rivera | A61J 1/00 |
| 2019/0091397 | A1* | 3/2019 | Macri | A61M 5/1415 |

OTHER PUBLICATIONS

"IV stand designed for children aims to reduce anxiety and improve hospital experience"; Website; dated Jul. 2, 2018; 6 pages; last accessed Jul. 16, 2023 at https://www.lboro.ac.uk/news-events/news/2018/july/student-designs-child-friendly-iv-stand/.

* cited by examiner

DISCREET HEALTH SYSTEM AND APPARATUS FOR INTRAVENOUS INFUSION EQUIPMENT

CROSS-REFERENCE TO RELATED APPLICATIONS

The present disclosure claims the benefit of U.S. Provisional Application No. 63/305,865 filed on Feb. 2, 2022, the contents of which are hereby incorporated herein in entirety.

FIELD OF INVENTION

The present disclosure provides for a medical equipment setup. In particular, one or more embodiments of the present disclosure relate to at-home intravenous infusion setups configured to resemble an object that is not medical equipment.

BACKGROUND

As the medical sciences advance, certain medical treatments are becoming more widespread and easier to perform to the point that the supervision of a medical professional is no longer required. Without the need to have a medical professional present in conjunction with expensive and overcrowded hospitals, it may be more desirable to perform the treatment in a location more convenient for the patient, including, but not limited to, their home, their place of employment, or their educational institution. Such treatments may include, but are not limited to, regular injections, glucose monitoring, and intravenous fluid and medication delivery. Patients performing such treatments on themselves likely do not enjoy the treatment for various reasons. For example, if the patient is performing the treatment in a public place, the equipment might draw unwanted attention, or if the patient has the medical equipment in their home, they may feel it seems out of place or that it ruins their desired aesthetic theme.

Further, there are patients being treated in hospitals in which the patient is experiencing extreme unease to the point that the overseeing medical professionals believe it would be in the patient's best interest to be in a more relaxed or comfortable setting. While many patients may require a more relaxed and comfortable environment for treatment, specific examples include, but are not limited to, sick children, the terminally ill, and those with ailments requiring them to spend weeks, months, or even years in the hospital. One possible reason these patients are feeling such extreme unease may be a feeling of being trapped and disdain for their environment because they are surrounded by numerous machines and other devices that constantly remind them of where they are or their condition forcing them to be there.

There is, therefore, an unmet need to create a comfortable environment for patients in their place of treatment. The present disclosure addresses such a need, among others.

SUMMARY

A system for concealing medical equipment causing the medical equipment to appear as another object or follow a design scheme more desirable to the user is provided. In one or more embodiments, the present disclosure provides for an apparatus for concealing intravenous infusion equipment consisting of a housing unit defining a cavity therein and having a concealing member, wherein the housing unit is configured to conceal an object on the housing unit or at least partially in the cavity of the housing unit. The apparatus may have a telescoping pole having a base sleeve coupled to the housing unit and an extending arm movably coupled to the base sleeve. The extending arm is configured to move relative to the base sleeve. The apparatus may have at least one intravenous bag hook coupled to a distal end of the extending arm.

One embodiment of the present disclosure is a system for concealing intravenous infusion equipment. The system conceals the intravenous infusion equipment while the telescoping pole is in the collapsed position by hiding the intravenous infusion equipment behind or within a concealing member and/or the cavity of the housing unit. In the same or other embodiments, the intravenous infusion equipment is substantially free from interference by the housing unit and concealing member while the telescoping pole is in the extended position.

Yet another embodiment of the present disclosure is a system for disguising intravenous infusion equipment. The system disguises the intravenous infusion equipment by incorporating both the intravenous infusion equipment and housing unit into the concealing member causing the system to appear as something else or follow a more desirable design scheme while the telescoping pole is in either the collapsed or extended position.

One aspect of this disclosure is a discrete medical system which can conceal the medical apparatus as another object or follow a design scheme that is more desirable to the user. The medical system functions as an intravenous infusion setup. The present disclosure involves several embodiments where the intravenous infusion setup can be configured to resemble a variety of different home décor items. In one or more embodiments, the present disclosure provides for an apparatus that conceals intravenous infusion equipment. The disclosure consists of a housing unit, defined as having a centralized cavity therein, with a telescoping concealing-member, a cylinder apparatus, extending from the cavity.

DETAILED DESCRIPTION

Figure 1B:
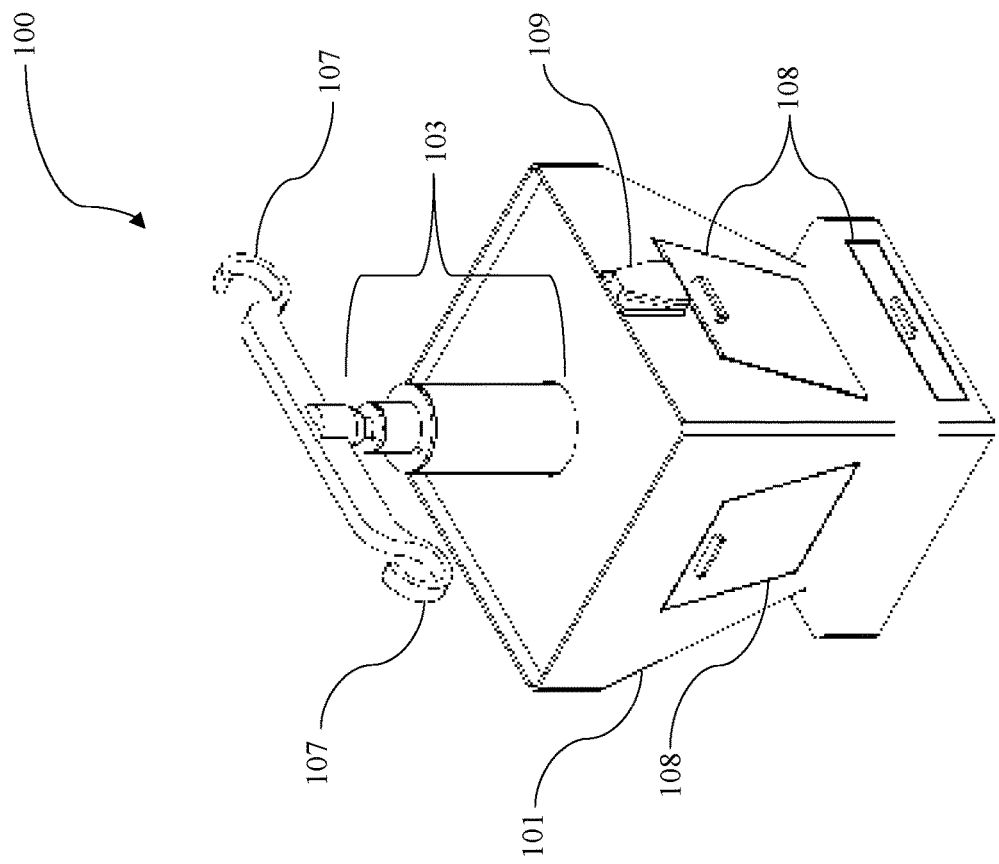
FIG. 1B is an elevated perspective of the embodiment illustrated in FIG. 1A.

For the purposes of promoting an understanding of the principles of the present disclosure, reference will now be made to the embodiments illustrated in the drawings, and specific language will be used to describe the same. Thus, the present disclosure is not intended to be limited to the embodiments shown, but is to be accorded the widest scope consistent with the principles and features described herein. It will nevertheless be understood that no limitation of the scope of this disclosure is thereby intended.

The present disclosure relates to a system for concealing medical equipment and more particularly, intravenous infusion equipment. In particular, embodiments considered herein relate to concealing intravenous infusion equipment by either hiding the intravenous infusion equipment from view or disguising the intravenous infusion equipment in order to appear as another object or to follow a more desirable design scheme for the user.

Figure 1A:
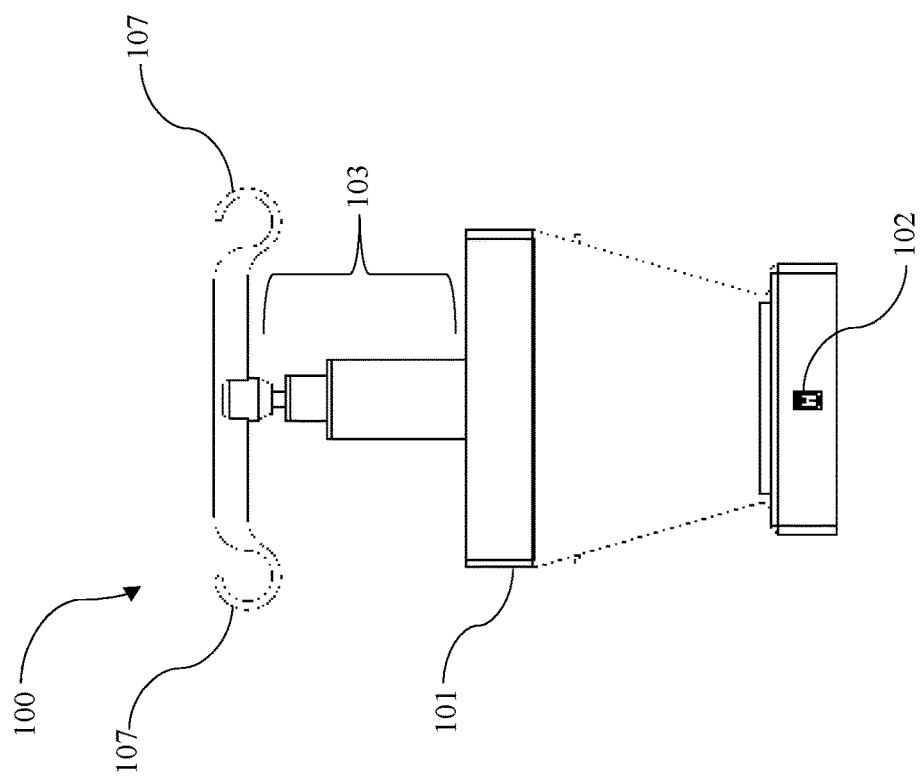
FIG. 1A is a schematic side view of an intravenous pump stand in the collapsed position, in accordance with one or more embodiments.
Figure 1C:
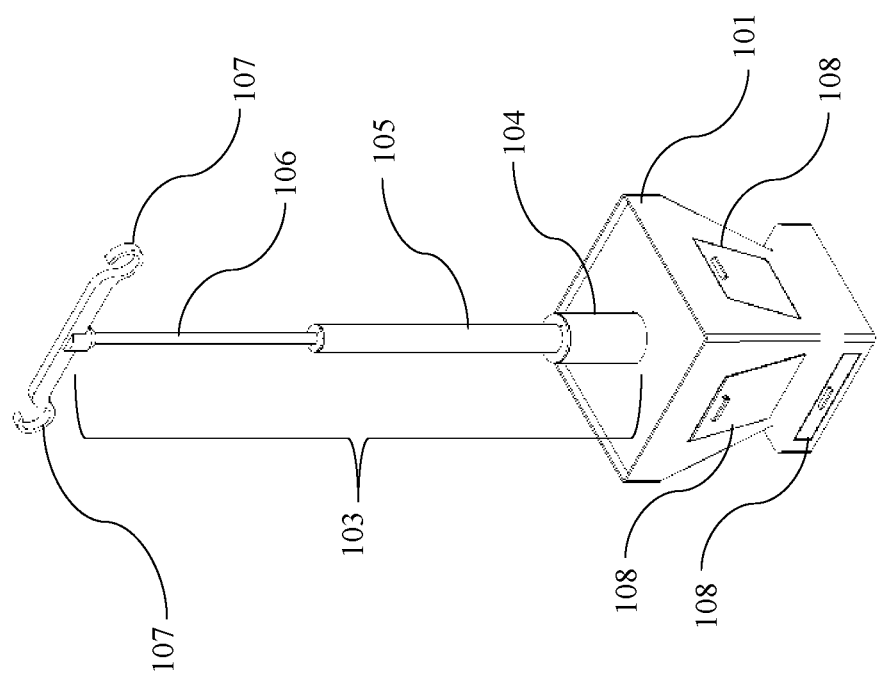
FIG. 1C is an elevated perspective of the embodiment of FIG. 1A in the extended position, in accordance with one or more embodiments.

FIG. 1A and FIG. 1B illustrate an intravenous system 100 in the collapsed position, and FIG. 1C illustrates the intravenous system 100 in the extended position, in accordance with one or more embodiments of the present disclosure. The intravenous system 100 has a housing unit 101 defining a cavity 108 therein, a telescoping pole 103 extendable to the extended position and having a base sleeve 104 coupled to the housing unit 101, an intermediate sleeve 105 coupled to the distal end of the base sleeve 104, an extending arm 106 coupled to the distal end of the intermediate sleeve 105, and at least one intravenous bag hook 107 coupled to the distal end of the extending arm 106.

The intravenous system 100 shown in the collapsed position includes, on the housing unit 101, an intravenous pump mount 109 and an activation mechanism 102 configured to control the telescoping pole 103. In one or more embodiments, the defined cavity or cavities 108 within the housing unit may be used as storage locations for any medical equipment or other supplies necessary for the use of the intravenous infusion equipment. Such medical equipment or supplies include, but are not limited to, an intravenous pump, bandages, or alcohol swabs. In another embodiment, the cavity may be used by the telescoping pole 103 to retreat at least partially within the housing unit 101 in order further conceal the intravenous infusion equipment. Further still, one embodiment utilizes the cavity 108 for both a storage location for supplies and to partially house one or more components of the telescoping pole 103.

Figures 2A, 2B:
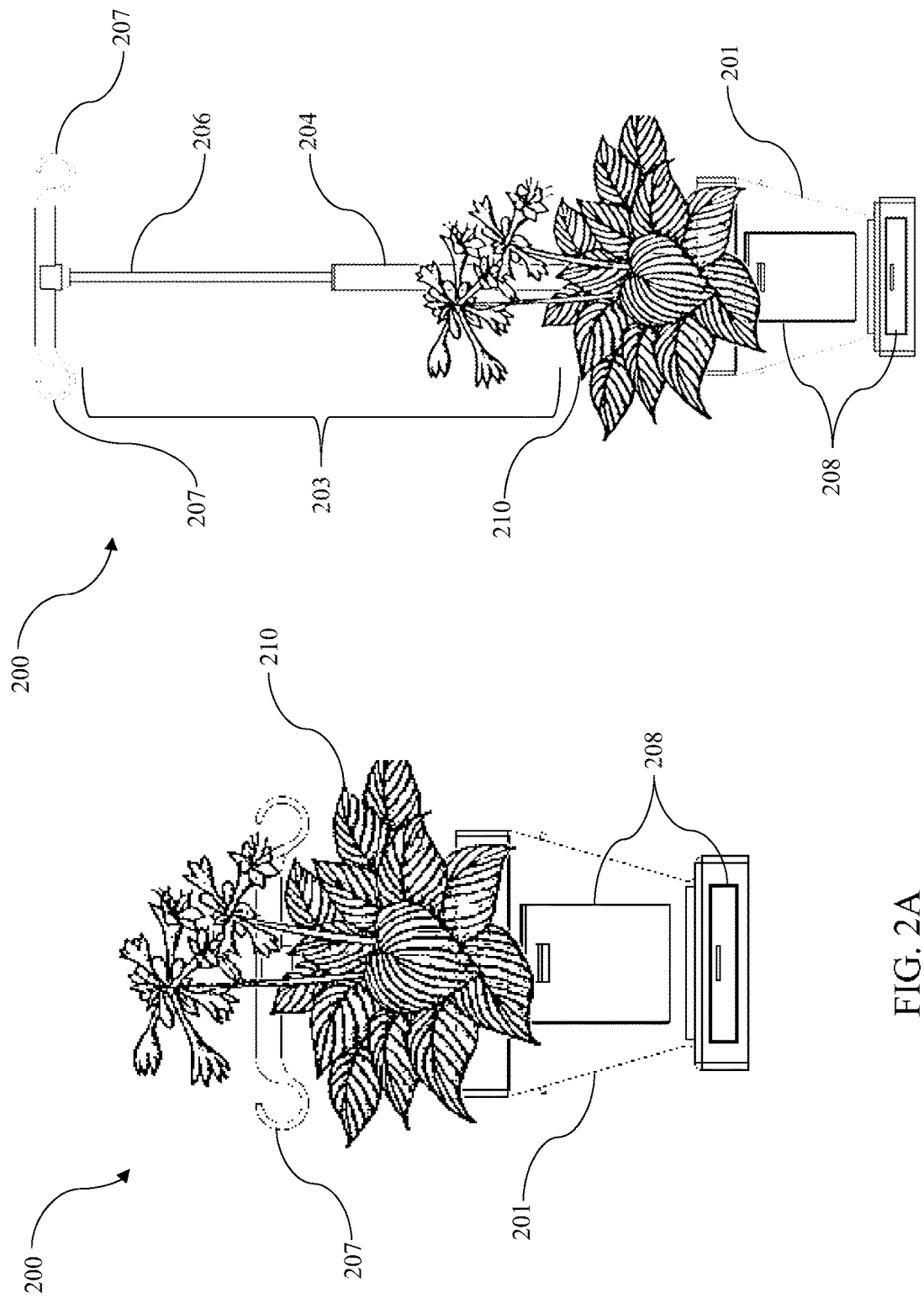
FIG. 2A is a side view of a discreet health system appearing as a table-top planter in the collapsed position, in accordance with one or more embodiments.
FIG. 2B is a side view of the discreet health system of FIG. 2A in the extended position, in accordance with one or more embodiments.

FIG. 2A and FIG. 2B illustrate another embodiment of a discreet intravenous system 200 in the collapsed position (FIG. 2A) and the extended position (FIG. 2B) respectively. The housing unit 201, defining a cavity 208, in one embodiment of the present disclosure, may have a concealing member 210 disposed thereon, wherein the concealing member is used to conceal a telescoping pole 203, the telescoping pole comprising a base sleeve 204 and an extending arm 206, and at least one intravenous bag hook 207 by at least partially hiding, or at least partially obscuring from view, the telescoping pole 203 and at least a portion of one intravenous bag hook 207. In one embodiment, the concealing member 210 comprises fake foliage which, while in the collapsed position, completely or partially obscures from view the telescoping pole 203 and at least a portion of one intravenous bag hook 207. In a preferred embodiment, the housing unit 201 is configured to appear as a container for the fake foliage in order to create the illusion of an ordinary house plant while in the collapsed position. In the same or another embodiment, the intravenous bag hooks 207 are coupled to the distal end of the telescoping pole 203 via pin joints to allow the intravenous bag hooks 207 to fold down while in the collapsed position to further hide them behind the foliage or concealing member 210. It will be appreciated by those skilled in the art that the concealing member 210 may be designed as any object generally found in the house in order to disguise the medical nature of the equipment. In other embodiments considered herein, the concealing member 210 and housing unit 201 may appear as a portrait, a piece of furniture, or a knife block among other things.

From FIG. 2B, in accordance with one or more embodiments of the present disclosure, the discreet intravenous system 200 is shown in the extended position. In one embodiment, the at least one intravenous bag hook 207 is sufficiently raised above the concealing member 210 so that a user may interact with the intravenous bag hook 207, such as placing an intravenous bag on the intravenous bag hook and then continuing to use said intravenous bag, without substantial interference from the housing unit 201 or the concealing member 210. It will be appreciated by those skilled in the art that the use without substantial interference from the housing unit and concealing member includes the proper use by the user as prescribed by their overseeing medical professional.

Figure 3A:
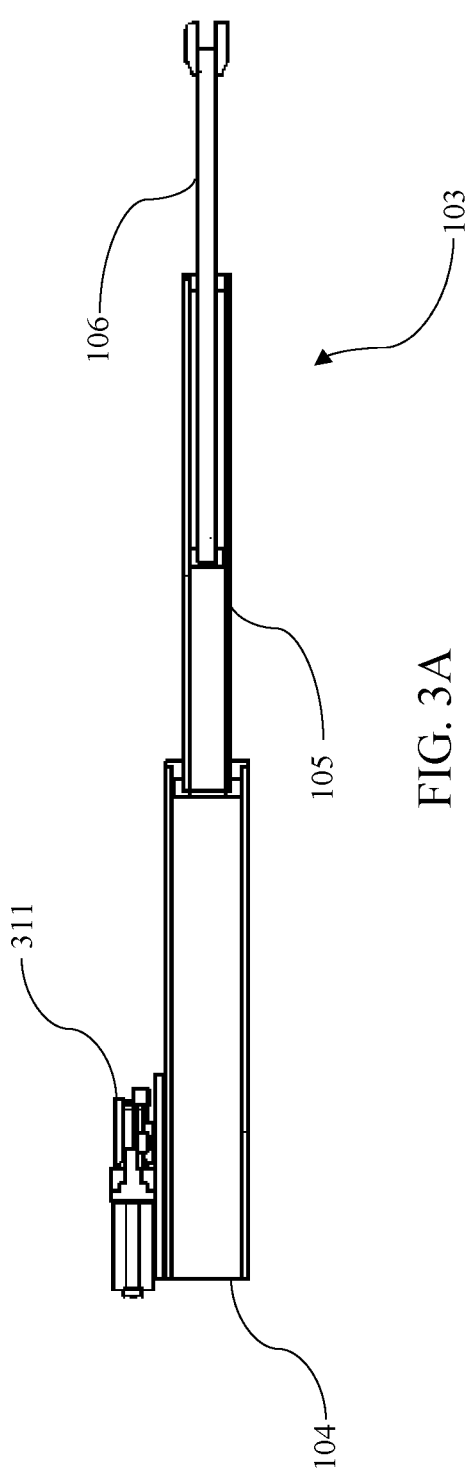
FIG. 3A is a section view of a telescoping pole, in accordance with one or more embodiments.
Figure 3B:
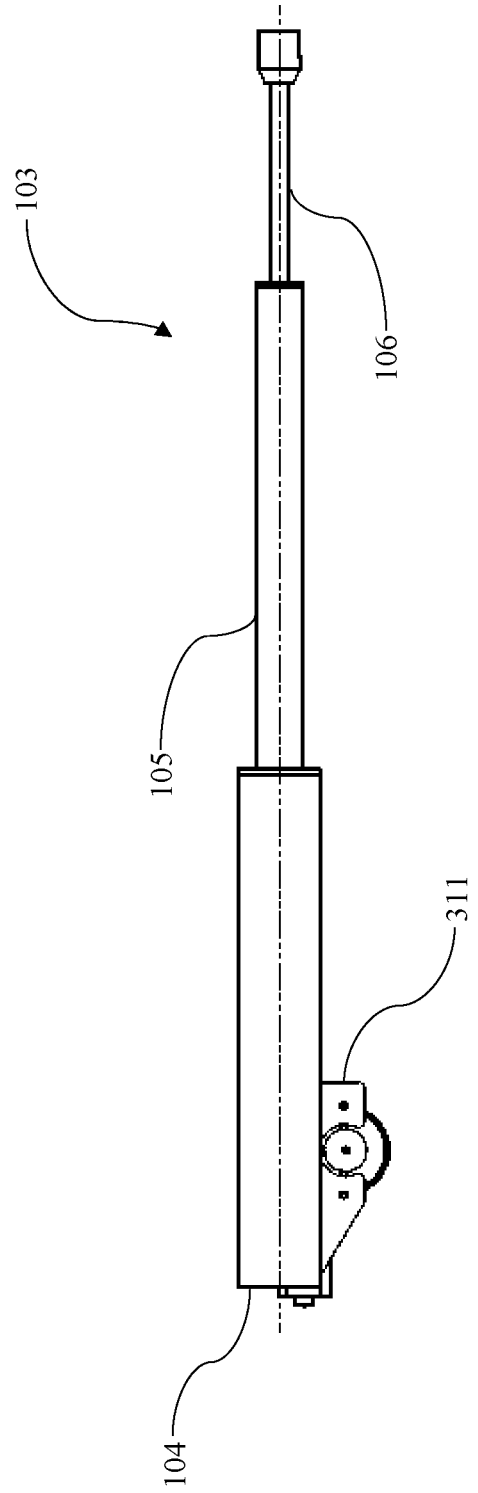
FIG. 3B is an offside view of the telescoping pole from FIG. 3A, in accordance with one or more embodiments.

FIG. 3A and FIG. 3B illustrated the telescoping pole 103 from a cross-sectional view (FIG. 3A) and a side view (FIG. 3B) respectively, in accordance with one or more embodiments of the present disclosure. In one example of this disclosure, the telescoping pole 103 comprises the extending arm 106 with a proximal end coupled to the distal end of the intermediate sleeve 105, a proximal end of the intermediate sleeve 105 coupled to the distal end of the base sleeve 104, and a motor 311 configured to actuate the telescoping pole 103 back and forth between the collapsed position and the extended position. One skilled in the art would recognize the placement of the motor could also be located on a different portion of the telescoping pole, a different location on the housing unit, or somewhere else entirely. Further, one skilled in the art would recognize the telescoping pole may serve a similar function if the intermediate sleeve was removed so that the extending arm was connected directly to the base sleeve or if multiple intermediate sleeves were used in the telescoping pole.

In one embodiment of the present disclosure, the motor 311 is configured to move the extending arm 106 coaxially with the intermediate sleeve 105 and the base sleeve 104 such that, while transitioning into the extended position, the motor extends the extending arm 106 until it is substantially out of the intermediate sleeve 105, at which point the extending arm 106 catches the intermediate sleeve 105 causing a tension force between the extending arm 106 and the intermediate sleeve 105. After the tension force occurs between the intermediate sleeve 105 and the extending arm 106, the motor 311 continues to actuate the extending arm 106 toward the extended position while the tension force causes the intermediate sleeve 105 to follow in the same direction until the intermediate sleeve 105 catches on the base sleeve 104, which is fixed to the housing unit 101, in the fully extended position.

In one or more embodiments of the present disclosure, while in the collapsed position, the extending arm is at least partially within the intermediate sleeve and the intermediate sleeve is at least partially within the base sleeve, and, while in the extended position, the intermediate sleeve is substantially extended from the base sleeve and the extending arm is substantially extended from the intermediate sleeve.

Figure 4B:
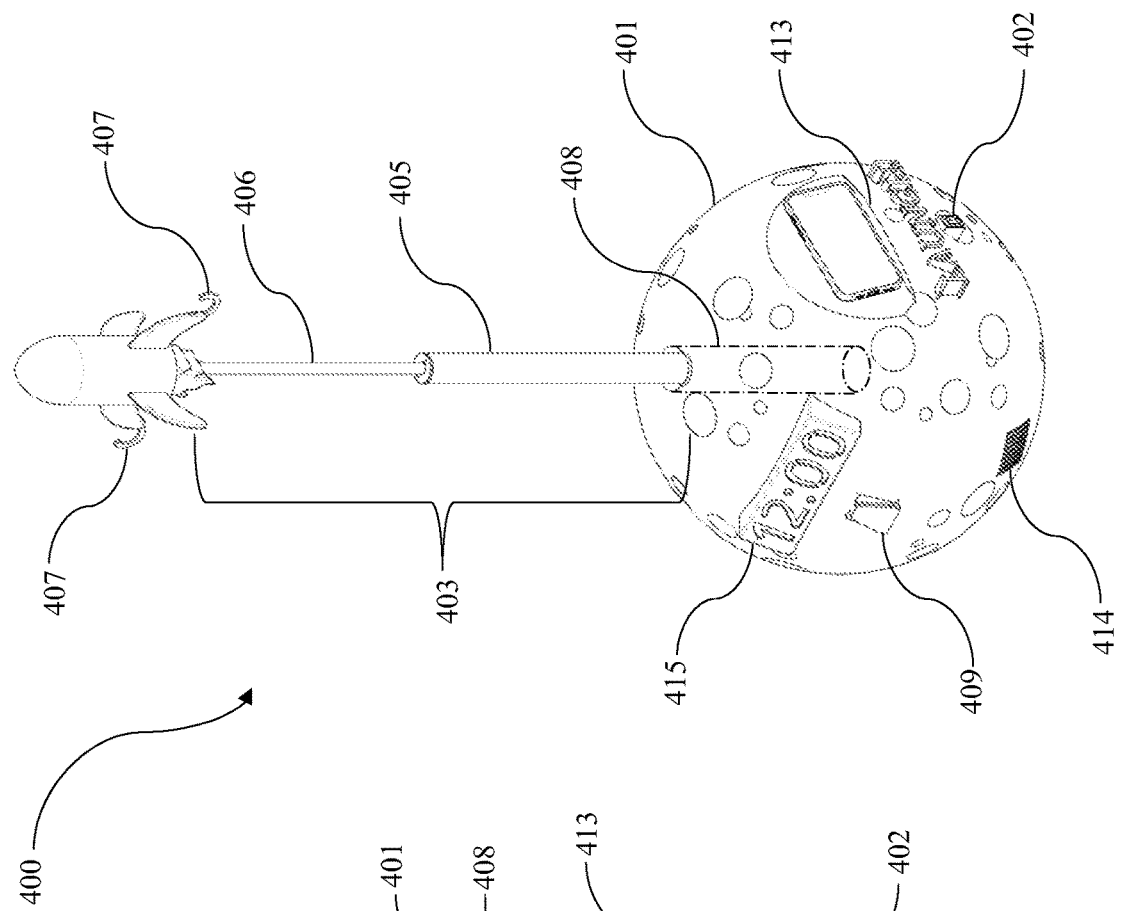
FIG. 4B is an elevated perspective view of the discreet health system of FIG. 4A in the extended position, in accordance with one or more embodiments.
Figure 4A:
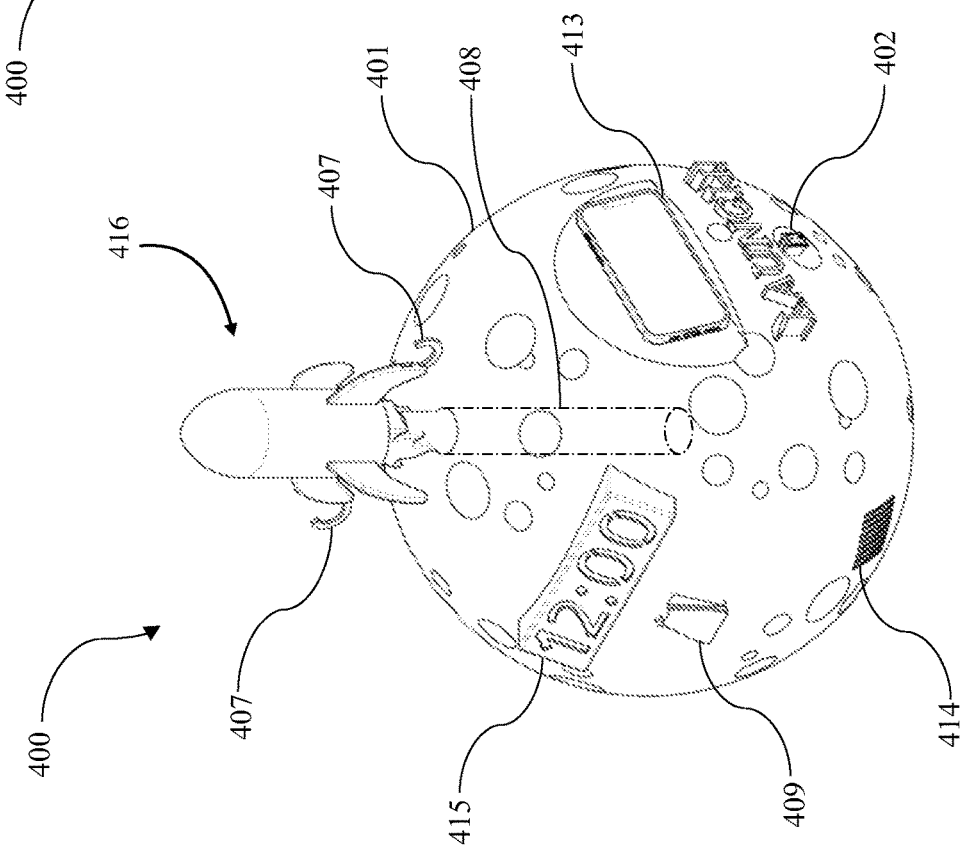
FIG. 4A is an elevated perspective view of a discreet health system appearing as a moon and spaceship in the collapsed position, in accordance with one or more embodiments.

In another embodiment of the present disclosure, as seen in FIG. 4A, the base sleeve and the cavity 408 within the housing 401 are the same element. In such an embodiment, the motor is configured to move the extending arm 406 and intermediate sleeve 405 coaxially with the cavity 408 so that, while in the collapsed position, the extending arm 406 and intermediate sleeve 405 are at least partially within the cavity 408 of the housing unit, and, while in the extended position, the extending arm 406 and the intermediate sleeve 405 are substantially raised out of the cavity 408. In another embodiment, the entirety of the telescoping pole and the intravenous bag hooks are within the cavity of the housing so that the telescoping pole and intravenous bag hooks are completely concealed from view.

One skilled in the art would appreciate the ability to use other methods and mechanisms besides a motor coupled to a pole with telescoping functions to extend the intravenous bag hook to a usable position. For example, the telescoping pole may be spring loaded and require the user to release a catch that allows the telescoping pole to extend on its own, and then, when no longer in use, the user would press the top of the pole toward the housing unit until the telescoping pole is sufficiently collapsed to the point it locks on the catch where it remains until future use. Another method of extending the intravenous bag hook to a usable position would be to utilize a lever arm instead of a telescoping pole where the intravenous bag hook is connected to the first end of the extending arm and the second end of the extending arm is connected via an elbow joint to the distal end of the base sleeve or intermediate sleeve. While in the collapsed position, the extending arm will be folded down to lie substantially parallel to the base sleeve. Transitioning to the extended position, the extending arm will swing about the elbow joint and away from the concealing member and housing unit until the intravenous bag hook is in a usable position.

FIG. 4A and FIG. 4B illustrate another embodiment of a discreet intravenous system 400 in the collapsed position and the extended position respectively. This embodiment comprises a housing unit 401, defining a cavity therein, with a time telling device 415, an intravenous pump mount 409, a speaker 414, an activation mechanism 402 and a telehealth stand 413, is provided for. The telehealth stand 413 is configured to allow an object of suitable size and shape to be propped up for the user to interact with during intravenous infusions. Such objects may include, but are not limited to, smartphones, tablets, or books. In such an embodiment, the entire discreet intravenous system 400 functions as the concealing member by disguising the intravenous infusion equipment and housing unit as a rocket blasting off from the moon or other object.

For example, a telescoping pole 403 may be topped with an ornamental feature 416 such as a rocket ship. At least one of the hooks 407 extending from the distal end of the telescoping pole 403 may extend from a portion of the ornamental feature 416 such as the fins of the rocket ship. Similarly, the housing unit 401 of the apparatus may embody an ornamental feature. For example, the ornamental feature of the housing unit 401 may resemble a plant pot, a portrait, a knife block, a piece of furniture, or a moon among other things.

While such a concealing technique would not hide the medical equipment from sight, it gives the medical equipment a design scheme that is more pleasurable to a user than a standard intravenous stand. This particular design scheme may be desirable for a child who experiences boredom while receiving an infusion for example.

Other such designs may be used based on the user's preferences. For example, the discreet intravenous system may be disguised as a giraffe where the housing unit is the giraffe's body, the telescoping pole is the giraffe's neck, the distal end of the extending arm is the giraffe's head, and the intravenous bag hooks are the giraffe's ears. Another such example of a similar design may utilize the trunk of an elephant for the telescoping pole while the intravenous bag hooks are configured to appear as water jets being shot from the elephant's trunk. It would be appreciated by one skilled in the art that any number of designs are possible, and this disclosure should not be read to not include other disguises.

One skilled in the art would appreciate the present disclosure's ability to conceal any medical equipment, not just intravenous infusion equipment, a user may wish to conceal or appear as something else entirely to fit their desired design scheme.

The present disclosure embodies a discrete medical device that appears as a familiar item to the user. Amongst other things, the device contains a cavity in the center of the base, with a collapsible telescoping pole vertically protruding from the cavity. This allows the pole to be rescinded at least partially into the base of the apparatus, giving it the user's desired appearance.

First, the telescoping pole is collapsible into the base of apparatus. To do this, the disclosure utilizes vertically extending segments that are all interconnected and can collapse in the same vertical direction on each other. This allows the pole to be extended and rescinded by the user or otherwise to provide the functionality of an intravenous administration device.

The base is structured as items that are ubiquitous to the environment in which the pole is placed. The base also functions as a weight and stabilizing tool for the larger apparatus. There is a motor unit attached to the base of the housing unit, allowing the pole to be extended and rescinded at the user's discretion.

In the present disclosure the term "conceal" is intended to mean at least partially hide, partially obscure, or disguise as something else.

In the present disclosure, the term "user" is intended to mean the entity, preferably human, who is using a device.

Those skilled in the art will recognize that numerous modifications can be made to the specific implementations described above. The implementations should not be limited to the particular limitations described. It will be appreciated by those skilled in the art that other implementations may be possible and are intended to be included within the present disclosure.

The invention claimed is:

1. An apparatus for disguising intravenous infusion equipment, comprising:
    a housing unit that is substantially spherical and configured to at least partially conceal a telescoping pole therein;
    the telescoping pole, comprising:
        a base sleeve moveably coupled to the housing unit,
        an extending arm movably coupled to the base sleeve, wherein the extending arm is configured to move relative to the base sleeve, and
        at least one hook coupled to a distal end of the extending arm.

2. The apparatus of claim 1, wherein the telescoping pole has a collapsed position wherein the extending arm is at least partially within the base sleeve; and
    wherein the extending arm is at least partially concealed by the housing unit in the collapsed position.

3. The apparatus of claim 1, further comprising an extend position wherein the at least one hook is sufficiently raised from the housing unit to allow a user to be able to interact with the at least one hook without substantial interference from the housing unit.

4. The apparatus of claim 1, wherein the telescoping pole further comprises at least one intermediate sleeve having a proximal end and distal end wherein the proximal end of the intermediate sleeve is moveably coupled to a distal end of the base sleeve and the distal end of the intermediate sleeve is moveably coupled to a proximal end of the extending arm; and wherein the base sleeve, the intermediate sleeve, and the extending arm move coaxially relative to one another.

5. The apparatus of claim 4, wherein the extending arm is at least partially within the intermediate sleeve and the intermediate sleeve is at least partially within the base sleeve while in the collapsed position.

6. The apparatus of claim 1, wherein the housing unit further comprises an intravenous pump mount.

7. The apparatus of claim 1, wherein the housing unit further comprises a telehealth stand.

8. The apparatus of claim 1, wherein the housing unit further comprises a speaker.

9. The apparatus of claim 1, wherein a motor is coupled to the housing unit, wherein the motor is configured to move the telescoping pole between an extend position and a collapsed position.

10. The apparatus of claim 1, wherein the base sleeve is at least partially concealed in the housing unit.

11. The apparatus of claim 1, wherein the telescoping pole is topped with an ornamental feature.

12. The apparatus of claim 11, wherein the at least one hook extending from the distal end of the extending arm extends from the ornamental feature.

13. The apparatus of claim 1, wherein the housing unit of the apparatus comprises an ornamental feature.

14. The apparatus of claim 13, wherein the ornamental feature resembles a moon.

15. An apparatus for disguising intravenous infusion equipment, comprising of:
a housing unit that is substantially spherical and configured to at least partially conceal a telescoping pole therein;
the housing unit further comprising of:
a time telling device, an intravenous pump mount, a speaker, an activation mechanism, and a telehealth stand;
the telescoping pole comprising:
a base sleeve coupled to the housing unit,
an extending arm movably coupled to the base sleeve, wherein the extending arm is configured to move relative to the base sleeve; and
an ornamental feature coupled to a distal end of the extending arm, having at least one hook coupled to the ornamental feature.

* * * * *